United States Patent [19]

Herman

[11] Patent Number: 4,637,719

[45] Date of Patent: Jan. 20, 1987

[54] OPTICAL MEASUREMENT OF MARINE CONDITIONS

[75] Inventor: Alex W. Herman, Lower Sackville, Canada

[73] Assignee: Canadian Patents and Development Limited, Ottawa, Canada

[21] Appl. No.: 641,044

[22] Filed: Aug. 14, 1984

[51] Int. Cl.$^4$ .................... G01N 21/85; G01N 21/59; G06M 11/04

[52] U.S. Cl. .................................. 356/72; 356/442; 377/11

[58] Field of Search ............................ 356/432–442, 356/73, 72; 377/10–12; 250/461.2

[56] References Cited

U.S. PATENT DOCUMENTS

| | | | |
|---|---|---|---|
| 3,800,147 | 3/1974 | Shea et al. | 356/442 X |
| 3,864,571 | 2/1975 | Stillman et al. | 250/461.2 X |
| 4,003,661 | 1/1977 | Yamano | 356/442 X |
| 4,080,076 | 3/1978 | Carr | 356/442 |
| 4,178,512 | 12/1979 | Frungel et al. | 250/461.2 |
| 4,225,245 | 9/1980 | Roiret et al. | 356/437 |
| 4,416,542 | 11/1983 | Mooradian | 356/442 X |

OTHER PUBLICATIONS

Herman, "In Situ Chlorophyll and Plankton Measurements with Batfish Vehicle", 1977, IEEE.

Herman and Mitchell, "Counting and Identifying Copepod Species with an in situ Electronic Zooplankton Counter", Deep-Sea Research, vol. 28, No. 7, pp. 739-755, 1981.

Dauphinee, "Zooplankton Measurements Using a Conductive Cell", Oceans '77.

Herman & Dauphinee, "Continuous and Rapid Profiling of Zooplankton with an Electronic Counter Mounted on a Batfish Vehicle", Deep-Sea Research, vol. 27A, pp. 79 to 96, 1980.

Primary Examiner—Vincent P. McGraw

[57] ABSTRACT

The apparatus provides a method of observing a water sample that is caused to flow rapidly past a beam of light of rectangular cross section. Attenuation of the beam by the sample is measured in a first detector that generates an output signal that has a basic, relatively slowly changing (e.g. half a second) component representative of the overall turbidity of the sample, and a series of short (e.g. 6 millisecond) pulses caused by individual, larger particles in the sample. The basic component is fed to a feedback circuit which so controls the light source as to maintain such component substantially constant. The intensity of the light source then provides a measure of the turbidity. A second detector counts the number of pulses above a certain threshold magnitude. In addition, this second detector can momentarily (during the occurrence of such a pulse) open a switch to prevent the feedback circuit from receiving the output signal of the first detector and hence avoid its reacting to the pulse. During this switched off time the output of the feedback circuit is held substantially constant by a capacitor. In what is expected to be its most important application, the apparatus will be used with sea water samples to obtain simultaneous measurements of the concentration of phytoplankton (typically 1 to 10 $\mu$m in diameter), as reflected in the turbidity of the sample, and counts of zooplankton (typically 0.4 to 20 mm diameter) which can be individually detected as pulses and counted by the second detector. However, the apparatus can also be used for measuring other factors causing turbidity in water samples, e.g. the presence of small non-organic particles, while simultaneously counting larger particles, which can include small fish as well as zooplankton.

13 Claims, 4 Drawing Figures

OPTICAL MEASUREMENT OF MARINE CONDITIONS

BACKGROUND OF THE INVENTION

The invention relates to method and apparatus for optically measuring certain marine conditions.

Fisheries and research scientists require continuous information on the marine food chain which dominantly consists of (1) phytoplankton (typically 1 to 10 $\mu$m in diameter), (2) zooplankton (typically 0.4 to 20 mm in diameter) and (3) fish, where each becomes a food source for the next in ascending order. Phytoplankton and zooplankton are measured in the oceans and studied for their interrelationships and for their profound effect on fisheries. Information is required on their abundance and vertical and horizontal distributions in continental shelf waters, deep oceans and inland waters. Acquiring this data accurately, continuously and with wide spatial coverage with limited shiptime is a major sampling problem.

In the past the sampling of zooplankton has generally been accomplished by towing large plankton nets with a mouth opening of approximately 0.5-2.0 meters and lengths of approximately 3-6 meters. Sampling phytoplankton has generally been accomplished by lowering or towing electronic instruments such as a fluorometer or a light attenuance meter. The latter instrument is less accurate in measuring phytoplankton biomass than the former but does provide an accurate vertical profile of relative concentration.

Deployment of zooplankton sampler nets from ships is generally cumbersome, time consuming and provides limited spatial coverage. The nets clog with algae material and must be recovered after short tows of approximately 10 mins. Vertical information is generally lost, since all the sample is integrated in the net, although there are two designs of multiple stacked nets which can yield improved but still limited vertical information. Obtaining simultaneous data on zooplankton and phytoplankton is often not done, since it requires the addition of other instruments thereby increasing complexity and cost. Usually the solution is to take water bottle samples on station and measure the phytoplankton biomass (using fluorometric techniques) on deck.

SUMMARY OF THE INVENTION

One object of the present invention is to provide apparatus capable of simultaneously obtaining data on both phytoplankton and zooplankton, and moreover of doing so in a simplified manner that nevertheless affords improved reliability by comparison with the methods hitherto employed.

While, as indicated, the invention is primarily concerned with the measurement of phytoplankton and zooplankton densities, it can also be used for the determination of other marine life concentrations or counts, such as that of small fish, and even non-organic particulate matter (dirt, mud etc.) that may affect the turbidity of the water and hence the environmental conditions to which the marine life is exposed.

In its basic thrust the invention makes use of a single optical system for carrying out two measurements simultaneously, one measurement being a determination of the attenuance of light passed through a sample of the water under study, and the other being a count of discrete bodies in such sample.

Hence, in its method aspect, the invention can be defined as a method of simultaneously determining turbidity caused by small particles (e.g. as a measure of phytoplankton density) and the number of larger particles (e.g. as a measure of zooplankton density) in a body of water, comprising (a) generating a beam of light of substantially rectangular cross-section, (b) flowing a sample of said water through the beam in a direction substantially perpendicular to the direction of extent of such beam, (c) detecting the received intensity of the beam after passage through the sample and generating a signal representative of such received intensity, said signal having a basic component corresponding to the turbidity and short pulses corresponding to the passage of individual ones of said larger particles through the beam, (d) reacting to variations in said basic component in a manner to cause the transmitted intensity of the beam before passage through the sample to be varied in such a manner as to maintain said basic component at a substantially constant value, (e) measuring said transmitted intensity as a determination of the turbidity, and (f) counting the number of said pulses as a measure of the number of larger particles.

In addition to phytoplankton, the turbidity measurement can be used to determine the concentration of other very small particles, e.g. non-organic matter, while the count of larger particles can determine either the density of zooplankton or small fish, such as fingerlings.

In its structural aspect the invention consists of apparatus for carrying out such a method, i.e. apparatus for simultaneously (i) measuring the turbidity of a water sample caused by small particles therein, and (ii) counting larger particles in said sample, such apparatus comprising (a) means defining an observation chamber, (b) means for flowing the sample through said chamber, (c) a light source for generating a beam of light of substantially rectangular cross-section, (d) means for directing such beam across said chamber and through the sample in a direction substantially perpendicular to the direction of flow of the sample, (e) a first detector for receiving and measuring the intensity of the beam after passage through the sample and for generating an output signal having a basic component caused by said turbidity and short pulses caused by individual ones of said larger particles, (f) a feedback circuit having an input connected to said first detector to receive said output signal, said feedback circuit having an output connected to said light source and operating means connected to said input for varying said last mentioned output and hence the intensity of said light source to maintain the basic signal component at a substantially constant value, said feedback circuit having a time constant for responding to changes in said basic signal component that is long relative to the length of said pulses, (g) means for measuring the intensity of said light source as a measure of said turbidity, and (h) a second detector connected to said first detector to receive said output signal therefrom and to count the number of said pulses therein of at least a predetermined magnitude as a measure of the number of said larger particles.

To achieve these results it is preferable that the dimension of the beam in the direction of flow of the sample, e.g. about 2 cm, and the rate of travel of the sample through the beam, e.g. typically 3 meters per second and an overall operating range of about 1-5 meters per second, be such as to produce a traverse time for a larger particle (and hence a length for each of the pulses) of typically about 6 milliseconds with an overall operating range of about 4–20 milliseconds. This will compare with a time constant for the feedback means of the order of about half a second, i.e. typically a 100 times longer and never less than about 25 times longer.

Preferably the light employed, or at least that detected, is red light in the visible spectrum, e.g. having a wavelength of 640 nm (full-width at half-maximum of ±20 nm), because at this wavelength substantially all the ambient light will have been absorbed a few feet below the surface of the sea.

In the preferred form of apparatus for carrying out the method, there is an interconnection between the circuits designed to minimise any interference in the accuracy of the first measurement (turbidity) arising from the data that forms the basis of the second measurement, the count. For example, the feedback circuit can include a switch that can temporarily disconnect its input from the operating means. This switch can be operated by the second detector when it senses a pulse of at least a predetermined magnitude. For the short time that the operating means is thus disconnected, i.e. for the duration of a pulse, the operating means relies on storage means, e.g. a capacitor, to hold the output of the feedback circuit substantially constant. This arrangement avoids the feedback circuit reacting to the short term pulses, while permitting it to respond on a much longer time scale to the basic signal component that reflects any changes in the overall turbidity of the sample.

BRIEF DESCRIPTION OF THE DRAWINGS

An embodiment of the invention is illustrated in the accompanying drawings, in which.

DETAILED DESCRIPTION OF THE PREFERRED EMBODIMENT

Figure 1:
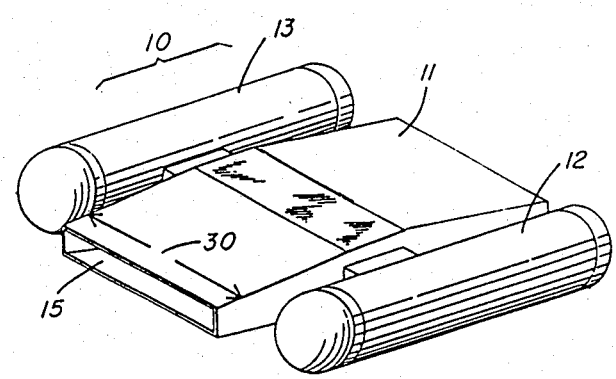
FIG. 1 is front top perspective of a submersible unit containing apparatus according to an embodiment of the present invention for determining plankton concentrations.
Figure 2:
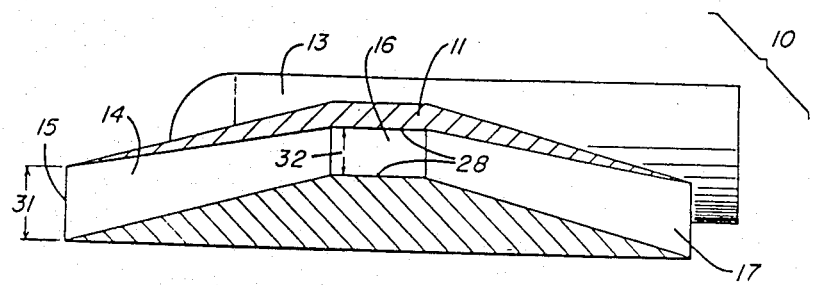
FIG. 2 is a simplified longitudinal central section, taken on a vertical plane, of the unit of FIG. 1.

The unit 10 is designed to be drawn through the sea or other body of water by conventional towing and depth regulating equipment (not shown). If desired, there can be a filtering net (not shown) to remove larger animals or particles ahead of the unit. As best seen in FIGS. 1 and 2 the unit 10 consists of a central body 11 connected to a pair of streamlined cylindrical side casings 12 and 13. The central body 11 serves to define a sampling tunnel 14 that extends from a mouth 15 through an observation chamber 16 to a discharge outlet 17. The pathway (14 to 16 to 17) is offset to prevent or at least mimimise direct light from reaching the detector, thus substantially eliminating the detection of ambient light. The left hand casing 12 contains the transmitting electronic and optical parts and the right hand casing 13 contains the receiving electronic and optical parts.

Figure 3:
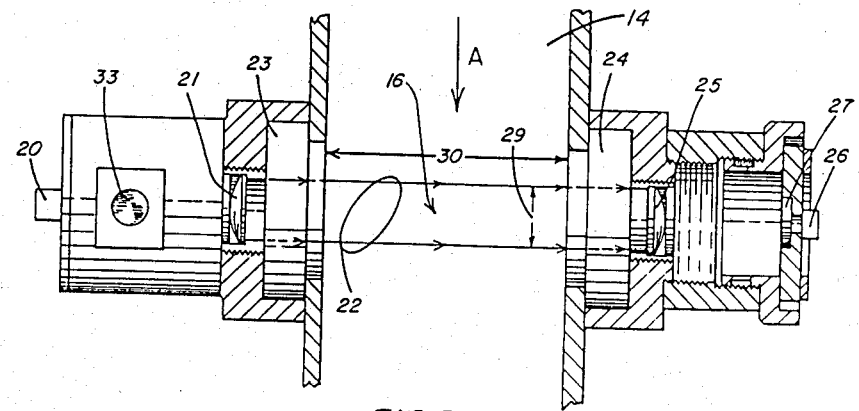
FIG. 3 is a simplified transverse central section, also taken on a vertical plane, of the unit of FIG. 1.

As best seen in FIG. 3, the optical transmitter or light source is an LED light bar 20 (here seen in end-on-view), the emission from which is collected by a lens 21 to form a beam 22 of square cross-section that passes through a glass plate 23 and across the observation chamber 16 to enter a second glass plate 24 and lens 25 to impinge on a photodiode 26 (also seen in end-on-view) after passing through a red filter 27 that cuts out the shorter wave lengths. As explained above, by excluding wave lengths shorter than about 620 nm, any interference from ambient daylight can be rendered insignificant.

In the specific apparatus illustrated, the beam formed by the lens will be square with, for example, height and width dimensions of 2.54 cm. However, as shown in FIG. 2, the sampling tunnel 14 is narrowed down from a height 31 at the mouth 15 of 3 cm to a height 32 at the chamber 16 of 2 cm. Thus the height of the beam that actually traverses the chamber 16 will be 2 cm and will completely fill the vertical dimension of that chamber. In addition, the top and bottom surfaces of the chamber 16 are each covered with a highly reflective surface layer 28, such as shiny aluminum foil or stainless steel plate, to avoid absorption of the light by the walls of the chamber. In its other transverse dimension, shown at 29 in FIG. 3, i.e. in the direction of water travel, as shown by the arrow A, the beam 22 will remain of full width, i.e. 2.54 cm. The length of the beam 22, i.e. the width 30 of both the mouth 15 and the chamber 16 is 20 cm throughout.

The transmitting casing 12 also houses a photodiode monitor 33 of known type that is located to one side of the passage from the light bar 20 to the lens 21, but is angled towards such light bar in a manner that enables it to receive sufficient light therefrom to be able to determine the intensity of such light source.

Figure 4:
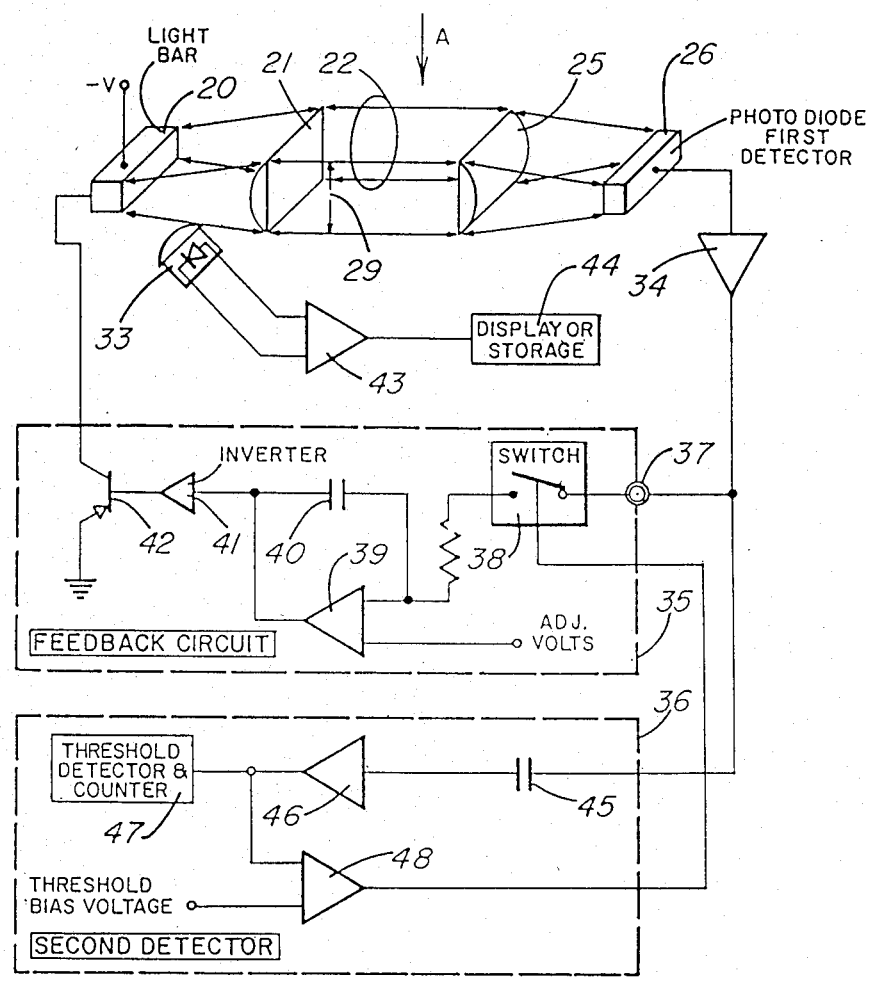
FIG. 4 is a circuit diagram illustrating the manner of operation of the apparatus.

The basic elements of the optical system are reproduced in FIG. 4 where the output of the photodiode 26, which acts as a first detector, is directed through an amplifier 34 to a feedback circuit 35 and to a second detector 36. Assuming that the unit 10 is used to simultaneously measure the turbidity of the water passing through the observation chamber 16, as a measure of biomass of small particles, e.g. phytoplankton, therein, and to count larger particles, e.g. zooplankton, individually, the output from the amplifier 34 will consist of a basic component representative of the turbidity and short pulses caused by the individual larger particles. The basic component will vary slowly and will thus be virtually a D.C. signal, while the short pulses will each have a length of the order of about 10 milliseconds, i.e. the time taken for a larger particle to traverse the dimension 29 of the beam 22 at a typical towing speed, e.g. 3–4 meters per second.

The feedback circuit 35 consists essentially of an input at terminal 37 connected through a switch 38 to operating means in the form of an integrating amplifier 39 with a parallel storage capacitor 40, inverter 41 and output transistor 42 connected to the light bar 20. This operating means will have a relatively long time constant, e.g. of the order of about half a second. Thus, this time constant is at least an order of magnitude, e.g. 25–100 times, longer than the length of each short pulse. If the light source 20 were kept constant, any increase in turbidity of the water would lower the basic component of the signal received at the input 37. The feedback circuit 35 would then function to increase the output of the bar 20 to restore the level of the light received by the photodiode 26, i.e. the so-called "received" intensity of the beam, and hence the level of the basic component of the output signal from the amplifier 34. The AC voltage at terminal 37 would therefore remain constant.

The photodiode 33 will detect the increase of the intensity of the light source 20, i.e. the so-called "transmitted" intensity of the beam, to generate an output through an amplifier 43 to a suitable display 44 or storage that thus provides the desired information, i.e. the degree of light attenuation arising from the turbidity level of the water.

The second detector 36 is connected to receive the output of the amplifier 34 at an input capacitor 45 that ensures effective A.C. coupling, i.e. excludes the D.C. basic component and admits only the short pulses. These are amplified in an amplifier 46 the output of which serves two functions. Firstly it is fed to a threshold detector and counting circuit 47 to provide a count of the number of pulses received of at least a certain magnitude. This magnitude can be preset in accordance with the expected size of the larger particles in the water and to exclude pulses that are mere noise. Occasionally an error can occur due to two such larger particles traversing the observation chamber 16 simultaneously or substantially so, but such error can normally be estimated and allowed for in the interpretation of the results. The second function of the output of the amplifier 46 is to control a further threshold detector (voltage comparator) 48 that is connected to the switch 38 to open it momentarily when a pulse of a predetermined magnitude is detected. The opening of this switch 38, which is a preferred but not essential feature of the present invention, further ensures that the function of the feedback circuit 35 will not be falsely influenced by the short pulses in the output of the amplifier 34. During the short time that the switch 38 is open, the output of the amplifier 39 is maintained substantially constant by the capacitor 40.

I claim:

1. A method of simultaneously determining turbidity caused by small particles and the number of larger particles in a body of water, comprising
   (a) transmitting in a predetermined direction a beam of light of substantially rectangular cross-section having a transmitted intensity,
   (b) flowing a sample of said water through the transmitted beam in a direction substantially perpendicular to said transmitting direction,
   (c) detecting a received intensity of the beam after passage through the water sample and generating a signal representative of such received intensity, said signal having a basic component corresponding to the turbidity of the water sample and short pulses each corresponding to passage through the beam of an individual one of said larger particles in said water sample,
   (d) causing variations in said basic component to modify the transmitted intensity of the beam before passage through the water sample in such a manner as to maintain said basic component at a substantially constant value,
   (e) measuring said transmitted intensity as a determination of said turbidity, and
   (f) counting the number of said short pulses as a measure of the number of said larger particles.

2. A method according to claim 1, wherein the turbidity indicates the density of phytoplankton in the sample and the number of larger particles is a measure of the density of zooplankton in the sample.

3. A method according to claim 1, wherein the time constant of said modifying of the transmitted intensity of the beam is at least an order of magnitude larger than the length of each said short pulse.

4. A method according to claim 3, wherein said time constant is at least half a second and said short pulses are each of the order of 6 milliseconds in length.

5. A method according to claim 1, wherein the received intensity of the beam detected is substantially restricted to visible red light.

6. A method according to claim 1, including inhibiting said modifying of the transmitted intensity of the beam during the presence of a said short pulse.

7. A method according to claim 6, including maintaining said transmitted intensity substantially constant during a said inhibiting step.

8. Apparatus for simultaneously
   (i) measuring the turbidity of a water sample caused by small particles therein, and
   (ii) counting larger particles in said water sample,
   such apparatus comprising
   (a) means defining an observation chamber,
   (b) means for flowing the water sample through said observation chamber,
   (c) means for generating a beam of light of substantially rectangular cross-section,
   (d) means for directing such beam across said observation chamber and through the water sample in a direction substantially perpendicular to the direction of flow of the water sample,
   (e) a first detector for receiving and measuring the intensity of the beam after passage through the water sample and for generating an output signal having a basic component representative of said turbidity and short pulses each caused by passage through the beam of an individual one of said larger particles,
   (f) a feedback circuit having an input connected to said first detector to receive said output signal, said feedback circuit having an output connected to said means for generating a beam of light and operating means connected to said input for varying said last mentioned output and hence the intensity of the generated beam to maintain the basic signal component at a substantially constant value, said feedback circuit having a time constant for responding to changes in said basic signal component that is long relative to the length of each said short pulse,
   (g) means for measuring the intensity of the generated beam as a measure of said turbidity, and
   (h) a second detector connected to said first detector to receive said output signal therefrom and to count the number of said short pulses therein of at least a predetermined magnitude as a measure of the number of said larger particles.

9. Apparatus according to claim 8, wherein said beam has a height extending across the full dimension of the observation chamber in the direction transverse to both the direction of travel of the beam and the direction of flow of the water sample through the observation chamber, whereby all said water sample must pass through the beam.

10. Apparatus according to claim 9, wherein inner walls of said chamber extending along and contacting the beam have reflective surfaces.

11. Apparatus according to claim 8, 9 or 10, wherein the width of said beam in the direction of flow of the water sample and the means for flowing the water sample through the beam, together produce a traverse time for a said small particle through the beam of the order of about 6 milliseconds, each of said short pulses having a length substantially equal to such traverse time, whereas the time constant of the feedback means is of the order of about half a second.

12. Apparatus according to claim 8, 9 or 10, wherein said first detector is sensitive primarily to visible red light.

13. Apparatus according to claim 8, 9 or 10, wherein (i) said feedback circuit includes switch means for disconnecting said input from said operating means, (j) said operating means includes storage means for holding said output of the feedback circuit substantially constant when said input is so disconnected, and (k) said second detector includes means connected to said switch means for momentarily actuating said switch means to disconnect the input upon detection of a said short pulse of at least a predetermined magnitude.

* * * * *